United States Patent
Jacobs

(10) Patent No.: US 11,167,021 B2
(45) Date of Patent: Nov. 9, 2021

(54) **VACCINE FOR PROTECTION AGAINST *STREPTOCOCCUS SUIS***

(71) Applicant: Intervet Inc., Madison, NJ (US)

(72) Inventor: Antonius Arnoldus Christiaan Jacobs, Kessel (NL)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 16/634,768

(22) PCT Filed: Aug. 2, 2018

(86) PCT No.: PCT/EP2018/070946
§ 371 (c)(1),
(2) Date: Jan. 28, 2020

(87) PCT Pub. No.: WO2019/025517
PCT Pub. Date: Feb. 7, 2019

(65) Prior Publication Data
US 2020/0206336 A1    Jul. 2, 2020

(30) Foreign Application Priority Data
Aug. 3, 2017 (EP) .................... 17184626

(51) Int. Cl.
*A61K 39/09* (2006.01)
*A61K 39/00* (2006.01)
*A61K 39/38* (2006.01)
*A61K 39/02* (2006.01)

(52) U.S. Cl.
CPC ...... *A61K 39/092* (2013.01); *A61K 2039/545* (2013.01); *A61K 2039/552* (2013.01)

(58) Field of Classification Search
CPC .................................................. A61K 39/092
See application file for complete search history.

(56) References Cited

FOREIGN PATENT DOCUMENTS

| EP | 2949340 A1 | 12/2015 |
| WO | 2015181356 A1 | 12/2015 |
| WO | 2017005913 A1 | 1/2017 |
| WO | WO 2017/005913 | * 1/2017 |

OTHER PUBLICATIONS

EP Search Report for EP Application 171846264 dated Dec. 5, 2017, 6 pages.
International Search report for PCTEP2018070946 dated Sep. 24, 2018, 4 sheets.
Seele, J et al, The immunoglobulin M-degrading enzyme of *Streptococcus suis*, IdeSsuis, is a highly protective antigen against serotype 2, Vaccine, 2015, pp. 2207-2212, vol. 33 No. 19, Elsevier, EP.
Segura, M., *Streptococcuc suis* vaccines: candidate antigens and progress, Expert Review of Vaccines, 2015, pp. 1587-1608, 14(12).
Baums, C et al, Immunogenicity of an Autogenous *Streptococcus suis* Bacterin in Preparturient Sows and Their Piglets in Relation to Protection after Weaning†, Clinical and Vaccine Immunology, 2010, pp. 1589-1597, vol. 17, No. 10, WO.
Lapointe, L et al., Antibody response to an autogenous vaccine and serologic profile for *Streptococcus suis* capsular type 1/2, The Canadian Journal of Veterinary Research, 2002, pp. 8-14, 66.

\* cited by examiner

*Primary Examiner* — Gary B Nickol
*Assistant Examiner* — Lakia J Jackson-Tongue
(74) *Attorney, Agent, or Firm* — Michael D. Davis

(57) ABSTRACT

The present invention pertains to a vaccine comprising an IgM protease antigen of *Streptococcus suis*, for use in a method for protecting piglets having maternally derived anti-*Streptococcus suis* antibodies against *Streptococcus suis*, by administering the vaccine to the piglets at an age of at most 28 days, preferably before the piglets are weaned.

6 Claims, No Drawings

VACCINE FOR PROTECTION AGAINST STREPTOCOCCUS SUIS

CROSS-REFERENCE TO RELATED APPLICATIONS

This application is a national stage entry under 35 U.S.C. § 371 of PCT/EP2018/070946, filed on Aug. 2, 2018, which claims priority to EP Application 17184626.4, filed on Aug. 3, 2017, the content of PCT/EP2018/070946 is hereby incorporated by reference in its entirety.

The invention pertains to the protection of young piglets against a pathogenic infection with *Streptococcus suis*.

BACKGROUND OF THE INVENTION

*Streptococcus suis* is a commensal and opportunistic pathogen of swine. In particular under stress, the bacterium may elicit a pathogenic infection and induce disease. Under modern pig producing conditions, major stress is induced for example by weaning of piglets and transport of young piglets. This has made *Streptococcus suis* to become a major swine pathogen. It is also an emerging zoonotic agent of human meningitis and streptococcal toxic shock-like syndrome. *Streptococcus suis* is a well-encapsulated pathogen and multiple serotypes have been described based on the capsular polysaccharide antigenic diversity. *Streptococcus suis* uses an arsenal of virulence factors to evade the host immune system. Together, these characteristics have challenged the development of efficacious vaccines to fight this important pathogen. Recently, an overview article has been published regarding vaccines against *Streptococcus suis* (Mariela Segura: "*Streptococcus suis* vaccines: candidate antigens and progress, in *Expert Review of Vaccines*, Volume 14, 2015, Issue 12, pages 1587-1608). In this review, clinical field information and experimental data have been compiled and compared to give an overview of the current status of vaccine development against *Streptococcus suis* as outlined here below.

Currently used vaccines are mainly whole-cell bacterins. However, field reports describe difficulty in disease control and management, and specially "vaccine failures" are common. Carrier pigs are the primary source of infection, and both vertical and horizontal transmission are involved in spread of the disease within a herd. Mixing of carrier animals with susceptible animals under stressful conditions such as weaning and transportation usually results in clinical disease. Early medicated weaning and segregated early weaning practices do not eliminate *Streptococcus suis* infection. Therefore, effective control measures to prevent disease will hinge on prophylactic/metaphylactic procedures (where allowed) and on vaccination. Currently, field immunization efforts have focused on the use of commercial or autogenous bacterins. These vaccine strategies have been applied to either piglets or sows. From weaning and onwards piglets are more susceptible to *Streptococcus suis* infections due to the stresses associated with weaning and also, the common subsequent transport. Therefore, prepartum immunization in sows is often used to try and convey passive immunity to piglets and provide protection against *Streptococcus suis* under these stressful circumstances early in life. Moreover, sow vaccination is less costly and labor intensive, thus representing an economical alternative to piglet vaccination. Yet, available results seem to indicate that sow vaccination with bacterins is also a matter of controversy. In many cases vaccinated sows, even when vaccinated twice before parturition, respond poorly or not at all to vaccination which results in low maternal immunity transferred to the litters. And even if maternal immunity is transferred at a sufficient level, in many cases the maternal antibodies are too low to provide protection in the most critical period of 4-7 weeks of age.

In piglets, autogenous bacterins are frequently used in the field, especially in Europe. They are prepared from the virulent strain isolated on the farm with clinical problems and applied to the same farm. One of the disadvantages of autogenous bacterins is that vaccine safety data are lacking and severe adverse reactions may occur. Sampling errors (due to using only one or two pigs or samples) may result in failure to identify a strain or serotype associated with a recent outbreak. This failure may be especially problematic in endemic herds. Finally, the most important dilemma of autogenous bacterins is that their actual efficacy has been poorly studied. As application of autogenous vaccines is empirical, it is not surprising that results obtained with these vaccines are inconsistent.

There is however another concern when vaccinating the piglets. In order to be protected right after weaning, the piglets need to receive their vaccine before weaning and thus, they need to receive the vaccine at a very young age, typically before they reach the age of 28 days. Active vaccination of such young animals has the concern of possible interference with maternal antibodies, either produced by natural infection or by active immunization of sows (Baums C G, Bruggemann C, Kock C, et al. "Immunogenicity of an autogenous *Streptococcus suis* bacterin in preparturient sows and their piglets in relation to protection after weaning", in: *Clin Vaccine Immunol*. 2010; 17:1589-1597). Indeed, neither vaccination of suckling nor of weaning piglets from immunized sows was associated with a prominent active immune response and protection at 8 weeks of age. This failure was associated with a strong inhibitory effect of maternal antibodies or other colostrum components. In this regard, interference between maternal antibodies and active production of antibodies against *S. suis* could also be demonstrated in a field study after vaccination with an autogenous *S. suis* capsular type 1/2 vaccine formulation (Lapointe L, D'Allaire S, Lebrun A, et al.: "Antibody response to an autogenous vaccine and serologic profile for *Streptococcus suis* capsular type 1/2." in: Can J Vet Res. 2002; 66:8-14. A field study aimed at determining the efficacy of a single-dose *S. suis* serotype 14 bacterin protocol in 4-day-old suckling piglets also failed to protect piglets against homologous challenge (Amass S F, Stevenson G W, Knox K E, et al. "Efficacy of an autogenous vaccine for preventing streptococcosis in piglets" in: Vet Med. 1999, 94, 480-484. Knowledge of antibody kinetics thus seems crucial before implementation of a rational vaccination program for piglets. The adopted strategy should allow minimal interference between passive maternal immunity and active immunization in piglets but maximal protection for pigs at the approximate time of onset of clinical signs, typically 2-3 weeks after weaning.

Other experimental vaccines are also described in the art. Kai-Jen Hsueh et al. show ("Immunization with *Streptococcus suis* bacterin plus recombinant Sao protein in sows conveys passive immunity to their piglets", in: *BMC Veterinary Research, BMC series—open, inclusive and trusted*, 13:15, 7 Jan. 2017) that a bacterin plus subunit might be a basis for successful vaccination of sows to confer protective immunity to their piglets.

Live attenuated vaccines have also been contemplated in the art. Non encapsulated isogenic mutants of *Streptococcus suis* serotype 2 have been clearly shown to be avirulent. Yet, a live vaccine formulation based on a non encapsulated serotype 2 mutant induced only partial protection against mortality and failed to prevent the development of clinical signs in pigs challenged with the wildtype strain (Wisselink H J, Stockhofe-Zurwieden N, Hilgers L A, et al. "Assessment of protective efficacy of live and killed vaccines based on a non-encapsulated mutant of *Streptococcus suis* serotype 2." in: *Vet Microbiol.* 2002, 84:155-168.)

In the last years, an extensive list of antigenic or immunogenic *Streptococcus suis* molecules has been reported, and most of these have been discovered through immuno proteomics using either convalescent sera from infected pigs or humans and/or laboratory-produced immune sera. WO2015/181356 (IDT Biologika GmbH) has shown that IgM protease antigens (either the whole protein or the highly conserved Mac-1 domain representing only about 35% of the full protein) can elicit a protective immune response in piglets in a vaccination scheme of administering two doses of the IgM protease antigen in combination with a prime vaccination containing a bacterin. It is not clear whether the IgM protease antigen alone is able to confer protective immunity. Next to this, the data only show successful vaccination in piglets having an age of 5-7 weeks and receiving a challenge infection at an age of 9 weeks, thus well after the risk period (i.e. the period of peak incidence of pathogenic *Streptococcus suis* infections) of 2-3 weeks after weaning, i.e. 5-7 weeks of age. There is no indication whether the IgM protease antigen is able to overcome the common problem of interference with maternal immunity. On the contrary, the choice of animals being vaccinated at an age of 5-7 weeks, is a clear indication that the interference with MDA's, if present, was meant to be avoided. So without any proof of effectiveness under practical circumstances (MDA's present during vaccination, and challenge infection in the window 2-3 weeks after weaning or transportation stress) it is still questionable whether the shown IgM protease/bacterin vaccine strategy is effective in practice. The same way, many licensed bacterin vaccines that are allowed on the market have inherently shown that they were effective in animal studies (otherwise they would not have been authorized to be commercially used), but they often fail to provide protection under practical, real-life circumstances. It is noted that WO2017/005913 (Intervacc AB) also describes the use of an IgM protease antigen (in particular, an IgM protease polypeptide fused to a nucleotidase) but only the property of being able to elicit a seroresponse has been shown. A protective effect for an IgM protease antigen is not shown in this international patent application.

OBJECT OF THE INVENTION

It is an object of the invention to find a vaccination strategy that is effective in protection of young piglets against *Streptococcus suis* (Ssuis), in particular against clinical signs associated with a pathogenic infection with this bacterium and/or mortality resulting therefrom, under the practical circumstances that the subject animals to be potentially vaccinated (i.e. the sows and/or their offspring) are seropositive for anti-Ssuis antibodies.

SUMMARY OF THE INVENTION

In order to meet the object of the invention a vaccine has been devised for administering to the piglets themselves, in particular a vaccine comprising an IgM protease antigen of *Streptococcus suis* (preferably comprising the IgM protease antigen as the only Ssuis specific antigen in the vaccine), for use in a method to (prophylactically) treat piglets having maternally derived anti-*Streptococcus suis* antibodies, by administering the vaccine to the piglets at an age of at most 28 days, to protect the piglets against *Streptococcus suis*. The age of vaccination with the IgM protease antigen can be any age of 1, 2, 3, 4, 5, 6, 7, 8, 9, 10, 11, 12, 13, 14, 15, 16, 17, 18, 19, 20, 21, 22, 23, 24, 25, 26, 27 or 28 days. As is known form the art, in particular from WO2017/005913, a positive immune response against an IgM protease antigen can be obtained in young piglets from the day of birth and onwards.

Surprisingly, it has been found that by using an IgM protease antigen (thus even when using only this Ssuis specific antigen in the vaccine), interference with maternal anti-Ssuis antibodies is not a problem for arriving at protection against *Streptococcus suis*, even when the piglets are vaccinated at an age of at most 28 days, and the animals are subject to a pathogenic infection with the bacterium at an early age, 2-3 weeks after weaning, induced by stress. This provides the unique option to vaccinate the piglets themselves and induce active protection, instead of relying on the short live passive protection that can be obtained via the colostrum of immunised mother animals. It has been shown that the vaccination may even take place before the piglets are weaned in order to have them protected against a disease resulting from *Streptococcus suis*, induced by the stress of weaning or the transportation of young animals right or soon after the weaning procedure. For the first time now, an antigen that was shown to have a protective effect in older animals, in which animals interference with MDA's is typically not a problem, has been shown to be useful for vaccinating MDA positive animals to arrive at a clear protective effect induced by stress at an early age, typically in the window of 2-3 weeks after weaning.

The invention also pertains to the use of an IgM protease antigen of *Streptococcus suis* for the manufacture of a vaccine for protecting piglets having maternally derived anti-*Streptococcus suis* antibodies against *Streptococcus suis*, by administering the vaccine to the piglets at an age of at most 28 days and to a method for protecting piglets having maternally derived anti-*Streptococcus suis* antibodies against *Streptococcus suis*, by administering a vaccine comprising an IgM protease antigen of *Streptococcus suis* to the piglets at an age of at most 28 days.

It is noted that in a vaccine the antigen is typically combined with a pharmaceutically acceptable carrier, i.e. a biocompatible medium, viz. a medium that after administration does not induce significant adverse reactions in the subject animal, capable of presenting the antigen to the immune system of the host animal after administration of the vaccine. Such a pharmaceutically acceptable carrier may for example be a liquid containing water and/or any other biocompatible solvent or a solid carrier such as commonly used to obtain freeze-dried vaccines (based on sugars and/or proteins), optionally comprising immunostimulating agents (adjuvants). Optionally other substances such as stabilisers, viscosity modifiers or other components are added depending on the intended use or required properties of the vaccine.

Definitions

A vaccine is a pharmaceutical composition that is safe to administer to a subject animal, and is able to induce protective immunity in that animal against a pathogenic microorganism, i.e. to induce a successful protection against the micro-organism.

An IgM protease antigen of *Streptococcus suis* is an enzyme that specifically degrades porcine IgM (and not porcine IgG or porcine IgA; Seele at al, in *Journal of Bacteriology*, 2013, 195 930-940; and in *Vaccine* 33:2207-2212; 5 May 2015), a protein denoted as IdeSsuis, or an immunogenic part thereof (typically having a length of at least about 30-35% of the full length enzyme). The whole enzyme has a weight of about 100-125 kDa, corresponding to about 1000-1150 amino acids, the size depending on the serotype of *S. suis*. In WO 2015/181356 several sequences that represent an IgM protease antigen of *Streptococcus suis* are given, viz. SEQ ID NO:1, SEQ ID NO:2, SEQ ID NO:6, SEQ ID NO:7 and SEQ ID NO:5, the latter being an immunogenic part of the full length enzyme (denoted as the Mac-1 domain, i.e. amino acids 80-414 of SED ID NO:7). Other examples of immunogenic parts of the full length enzyme are given in WO2017/005913. In particular the IgM protease may be the protease according to SEQ ID NO:1 of WO2015/1818356 or a protein having at least 90%, or even 91, 92, 93, 94, 95, 96, 97, 98, 99% up to 100% sequence identity in the overlapping regions. The amino acid sequence identity may be established with the BLAST program using the blastp algorithm with default parameters. It is expected that the IgM protease of *Streptococcus suis* of various serotypes have a sequence identity higher than 90%, in particular expected to be 91, 92, 93, 94, 95, 96, 97, 98, 99% up to 100%. An artificial protein, for example made to optimize yield in a recombinant production system of the antigen, may lead to a lower amino acid sequence identity such as 85%, 80%, 75%, 70% or even 60% compared with the whole enzyme, while maintaining the required immunogenic function, and is understood to be an IgM protease antigen of *Streptococcus suis* in the sense of the present invention.

Protection against a micro-organism is aiding in preventing, ameliorating or curing a pathogenic infection with that micro-organism or a disorder arising from that infection, for example to prevent or reduce one or more clinical signs resulting from the infection with the pathogen.

A vaccination method consisting of administering one shot of a vaccine means that protective immunity is conferred after only one single shot of the vaccine, and thus, that a booster vaccination is omitted to arrive at the said protective immunity. In a two-shot regime, the first (prime) vaccination is typically boosted within 6 weeks from the first administration, commonly within 3 or even 2 weeks from the first administration, and only after the second (boost) administration protective immunity, i.e. a successful protection as defined here above, is understood to be obtained.

EMBODIMENTS OF THE INVENTION

In a first embodiment of the present invention the method consists of administering one shot of the vaccine. Even more surprisingly, one shot of the vaccine appears to be capable of eliciting protective immunity in the MDA positive piglets. In the art, non-live *Streptococcus suis* vaccines have always been administered in a prime-boost regime, and still, led to relatively poor efficacy. Regarding the antigen for use in the current invention, the art (see WO2015/181356 and WO2017/005913) has consistently used this antigen in a two-shot administration approach. It was therefore highly surprising to see that even a single dose with a vaccine containing (only) an IgM protease as antigen, is able to induce protective immunity in animals that have antibodies against *Streptococcus suis*, in particular maternally derived antibodies.

In another embodiment the vaccine is administered before an age at which the piglets are weaned. In other words, the vaccine is administered before the piglets are actually weaned. It has been shown that the vaccination at this early age, can protect against a pathogenic infection with *Streptococcus suis*, induced by stress within a short window of 2-3 weeks right after weaning.

In yet another embodiment the vaccine is for conferring protection against clinical signs associated with a pathogenic infection with *Streptococcus suis*. Typical clinical signs associated with a pathogenic infection with *Streptococcus suis* are increased rectal temperature, impaired locomotion (limping, swollen joints), increased respiration rate and neurological signs (e.g. tremors, convulsions, torticollosis, ataxia). Preventing, amelioration are curing one or more of these signs will be beneficial for the pig, not only since it is an indication that the pathogenic infection is being suppressed.

In still another embodiment the vaccine is for conferring protection against an increased mortality associated with a pathogenic infection with *Streptococcus suis.*

In again another embodiment the IgM protease antigen is present in an amount below 250 μg per dosis of the vaccine, preferably below 120 μg per dosis of the vaccine. The minimum amount is the amount at which protective immunity can still be obtained. This can be established by routine experimentation and depends i.a. on the immunogenic properties of the IgM protease antigen chosen but also on the required level of protection. For the current vaccine, a minimum amount is believed to be 1 μg of the antigen per dosis, but it may be any higher dosis such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or any higher integer in the range 61-119 up to 120 μg per dosis.

The invention will now be further explained based on the following non-limiting examples.

EXAMPLES

Example 1

As protection against *Streptococcus suis* for piglets is required in the risk period (typically 4-7 weeks of age) it was assessed whether an IgM protease containing vaccine is efficacious as a one shot vaccine in antiSsuis positive piglets at an age of 3 weeks. The aim of the present study was to test whether the vaccine is efficacious as a one-shot vaccine (in two different formulations) in comparison to a regular bacterin vaccine.

Study Design

Thirty 3-week-old anti-Ssuis MDA positive piglets were used for the experiment. The piglets were allotted to three groups (evenly distributed over the different litters) of 10 piglets each. Group 1 was vaccinated once intramuscularly at 3 weeks of age with a recombinant rIdeSsuis IgM protease antigen (Seele et al: Vaccine 33:2207-2212; 5 May 2015, par. 2.2.) at 250 μg per dose (as established by a Bradford protein assay using BSA as a standard) in the commercially available Emulsigen adjuvant (Phibro Animal Health, Teaneck, USA). Group 2 was vaccinated once intramuscularly (2 ml) at 3 weeks of age with the recombinant rIdeSsuis IgM protease (250 μg per dose; Bradford protein assay using bovine serum albumin as a standard) in the commercially available X-Solve adjuvant (MSD Animal Health, Boxmeer, The Netherlands). Group 3 was vaccinated once intramuscularly at 3 weeks of age with a bacterin vaccine ($2\times10^9$ cells) in X-Solve, using inactivated *Streptococcus suis* serotype 2 bacteria, comparable to the antigen as present in the commercially available vaccine Porcilis Strepsuis (MSD Animal Health). At 4 weeks of age the piglets were weaned. At 6 weeks of age the piglets were transported to the challenge room and challenged immediately. There was no acclimatization period between the transport and the challenge to mimic natural stress. The piglets were challenged with a virulent culture of Ssuis serotype 2. After challenge the pigs were daily observed for clinical signs associated with a pathogenic Ssuis infection such as depression, locomotory problems, increased respiration rate and neurological signs using a regular scoring system going from 0 (no signs) to 3 for severe cases. The same scoring system (0 for parameter not visible, the highest number for severe cases) was used for the other parameters. Just before vaccination and challenge serum blood was collected for antibody determination using an experimental Ssuis antibody ELISA against whole cells. At regular times before and after challenge heparin blood was collected for re-isolation of challenge strain. At the end of the study (7 days after challenge) all surviving pigs were euthanized and post-mortem examined.

Results

None of the vaccines induced any unacceptable site or systemic reactions and thus could be considered safe. The post challenge data for the period before euthanisation (at day 7) are indicated in Table 1.

TABLE 1

Post challenge data

| Group | Survival time (d) | Peak temp (° C.) | Clinical score | Blood reisolation score |
|---|---|---|---|---|
| 1 | 5.4 | 40.6 | 27.2 | 1.9 |
| 2 | 5.9 | 40.5 | 17.8 | 1.4 |
| 3 | 3.2 | 41.2 | 59.2 | 4.7 |

The post-mortem scores for the joints (score going from 0 to 3 if fibrinous material is present), joint reisolation (score going from 0 to 4 when the amount of CFU is over 1000), the internal organs (score going from 0 to 3 for lungs and abdominal cavity/pleura and pericard and from 0 to 4 for Meninges) and organ reisolation (score going from 0 to 4 when the amount of CFU is over 1000) are given in table 2.

TABLE 2

Average post mortem scores

| Group | Joint | Joint reisolation | Internal organs | Organ reisolation |
|---|---|---|---|---|
| 1 | 0.8 | 6.1 | 2.0 | 7.1 |
| 2 | 0.4 | 3.4 | 1.4 | 4.4 |
| 3 | 5.3 | 17.4 | 4.2 | 13.9 |

Conclusion

All parameters were improved in the two IgM protease vaccine groups 1 (Emulsigen adjuvant) and 2 (X-Solve adjuvant) when compared to the bacterin group 3. The vaccine formulated in XSolve appeared to induce better protection than the vaccine as used in Group 1: all 8 parameters tested were significantly improved in group 2 as compared to group 3, and 3 of 8 parameters (viz. "survival time", "joint reisolation score" and "internal organs score") were significantly improved in group 1 as compared to group 3. In conclusion, the results demonstrate that a one-shot IgM protease subunit vaccine at 250 μg/dose induced protection in 3-week-old MDA positive piglets against a pathogenic infection with *Streptococcus suis* serotype 2, when challenged 3 weeks after vaccination, 2 weeks after weaning and immediately after transport.

Example 2

A second experiment was run which was basically the same as the first experiment (see here above under Example 1), using MDA positive piglets at an early age, before weaning, but wherein a lower dose of the IgM protease was used (120 μg per dose in each case), and wherein in a first group (Group1) an alternative Xsolve adjuvant was used (having the same constituents as the Xsolve adjuvant in Example 1 but only at 60% of the concentration thus being milder). Group 2 received the antigen formulated in the alum based adjuvant Emunade (MSD Animal Health, Boxmeer, The Netherlands). Group 3 served as a negative challenge control group. No positive control group was used in this experiment Other differences between the two experiments are that in this experiment the piglets are slightly older at day of vaccination (3% weeks) and 1 week older (7 weeks) at day of challenge.

The vaccines appeared to be safe after administration. The results of the challenge experiment are indicated here beneath.

TABLE 3

Post challenge data

| Group | Early euthanisations (#) | Peak temp (° C.) | Clinical score | Blood reis. score |
|---|---|---|---|---|
| 1 | 2/10 | 40.4 | 16.4 | 0.5 |
| 2 | 3/10 | 40.6 | 13.2 | 1.1 |
| 3 | 8/10 | 40.9 | 52.0 | 2.7 |

The results during the clinical phase indicate that all parameters are improved for each vaccine. The post-mortem data are indicated in Table 4. Also from the post-mortem data it appears that the vaccines, although at a lower dose and using milder adjuvants than the adjuvant used in the first experiment, are able to protect against *Streptococcus suis*. Based on these data it is believed that protection against *Streptococcus suis* can also be obtained when using a dosis below 120 μg, in particular a dosis between 1 and 120 μg according to a specific embodiment of the vaccine for use according to the invention as outlined here above.

TABLE 4

Average post mortem scores

| Group | Joint | Joint reisolation | Internal organs | Organ reisolation |
|---|---|---|---|---|
| 1 | 0.4 | 0.3 | 0.4 | 0.6 |
| 2 | 0.8 | 1.3 | 0.3 | 1.6 |
| 3 | 2.1 | 1.5 | 1.7 | 3.9 |

The invention claimed is:

1. A method for protecting piglets having maternally derived anti-*Streptococcus suis* antibodies against *Strepto*-

*coccus suis*, comprising administering a vaccine comprising an IgM protease antigen of *Streptococcus suis* to the piglets at an age of at most 28 days.

2. The method of claim 1, comprising administering one shot of the vaccine.

3. The method of claim 1, wherein the administering of the vaccine is before an age at which the piglets are weaned.

4. The method of claim 1, wherein the method is for conferring protection against clinical signs associated with a pathogenic infection with *Streptococcus suis*.

5. The method of claim 1, wherein the method is for conferring protection against an increased mortality associated with a pathogenic infection with *Streptococcus suis*.

6. The method of claim 1, wherein the IgM protease antigen is present in an amount below 250 μg per dose of the vaccine, preferably below 120 μg per dose.

* * * * *